(12) United States Patent
Korba et al.

(10) Patent No.: US 6,376,065 B1
(45) Date of Patent: Apr. 23, 2002

(54) FLUOROCHEMICAL BENZOTRIAZOLES

(75) Inventors: Gary A. Korba, Oakdale; Mark E. Mueller, Marine St. Croix; Robert A. Sinclair, St. Paul, all of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/666,359

(22) Filed: Sep. 20, 2000

Related U.S. Application Data

(63) Continuation of application No. 09/014,098, filed on Jan. 27, 1998, now abandoned.

(51) Int. Cl.$^7$ ................. B32B 15/04; C07D 249/18
(52) U.S. Cl. ................. 428/333; 428/411.1; 428/457; 548/257; 548/260; 548/261
(58) Field of Search ................. 428/421, 457, 428/333, 411.1; 548/257, 260, 261

(56) References Cited

U.S. PATENT DOCUMENTS

| | | | | |
|---|---|---|---|---|
| 3,082,088 A | * | 3/1963 | Heilmann et al. | 430/614 |
| 4,187,186 A | * | 2/1980 | Braid | 252/51.5 R |
| 4,788,292 A | * | 11/1988 | Clark et al. | 548/260 |
| 5,504,214 A | * | 4/1996 | Marhold et al. | 548/259 |

* cited by examiner

*Primary Examiner*—Paul Thibodeau
*Assistant Examiner*—Ramsey Zacharia
(74) *Attorney, Agent, or Firm*—Scott A. Bardell

(57) ABSTRACT

The invention provides compounds having the formula:

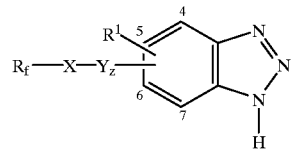

wherein $R_f$ is $C_nF_{2n+1}$—$(CH_2)_m$—, wherein n is 1 to 22 and m is 0, or an integer from 1 to 3; X is —$CO_2$—, —$SO_3$—, —CONH—, —O—, —S— a covalent bond, —$SO_2NR$—, or —NR—, wherein R is H or $C_1$ to $C_5$ alkylene; Y is —$CH_2$— wherein z is 0 or 1; and $R^1$ is H, lower alkyl or $R_f$—X—$Y_z$— with the provisos that when X is —S—, or —O—, m is 0, sand z is 0, n is $\geq 7$ and when X is a covalent bond, m or z is at least 1, and uses thereof.

31 Claims, 2 Drawing Sheets

FLUOROCHEMICAL BENZOTRIAZOLES

This is a continuation of application Ser. No. 09/014,098, filed Jan. 27, 1998, now abandoned.

FIELD OF THE INVENTION

This invention relates to fluorochemical benzotriazole compounds and uses thereof.

BACKGROUND OF THE INVENTION

Heretofore, there have been many ways to enhance the separation or release of one material from a surface of another material or substrate. For example, organic materials such as oils and waxes and silicones have been used as release agents to provide release characteristics to surfaces. One of the disadvantages of these release agents is that they usually need to be frequently re-applied to the surface so as to provide adequate release properties. Polymeric release coatings such as those made from polytetrafluoroethylenes have addressed some of the shortcomings of oils, waxes, silicones and other temporary coatings and are often more durable. Typically however, polymeric release coatings require a thicker coating than the non-durable treatments, they can be subject to thickness variations, and can present application difficulties.

SUMMARY OF THE INVENTION

The invention provides fluorochemical benzotriazoles that chemically bond to metal and metalloid surfaces and provide, for example, release and/or corrosion inhibiting characteristics to those surfaces. The compounds of the invention are characterized as having a head group which bonds to a metallic or metalloid surface and a tail portion which is suitably different in polarity and/or functionality from a material to be released. The compounds of the invention when applied to a metallic or metalloid surface form durable, self-assembled films that are monolayers or substantially monolayers. Fluorochemical benzotriazoles of the invention include those having the formula:

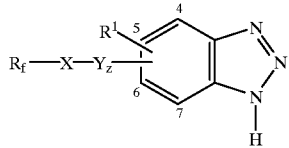

wherein $R_f$ is $C_nF_{2n+1}$—$(CH_2)_m$, wherein n is an integer from 1 to 22 and m is 0, or an integer from 1 to 3; X is —$CO_2$—, —$SO_3$—, —CONH—, —O—, —S—, a covalent bond, —$SO_2NR$—, or —NR—, wherein R is H or $C_1$ to $C_5$ alkylene; Y is —$CH_2$— wherein z is 0 or 1; and $R^1$ is H, lower alkyl or $R_f$—X—$Y_z$— with the provisos that when X is —S—, or —O—, m is 0, and z is 0, n is $\geq 7$ and when X is a covalent bond, m or z is at least 1. Preferably n+m is equal to an integer from 8 to 20.

This invention further provides compositions comprising one or more of the fluorochemical benzotriazoles.

This invention also provides a method of treating a metallic or a metalloid surface with a compound of the invention comprising the step of contacting a composition comprising a fluorochemical benzotriazole of the invention to the metallic or metalloid surface. An ultra-thin film can be formed on a surface by contacting the surface with a fluorochemical benzotriazole in liquid or vapor form.

This invention also provides fluorochemical benzotriazole compositions for use as release agents comprising one or more compounds having the formula:

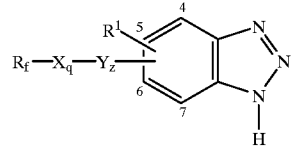

wherein $R_f$ is $C_nF_{2n+1}$—$(CH_2)_m$—, wherein n is 1 to 22, m is 0 or an integer from 1 to 3; X is —$CO_2$—, —$SO_3$—, —S—, —O—, —CONH—, a covalent bond, —$SO_2NR$—, or —NR—, wherein R is H or $C_1$ to $C_5$ alkylene, and q is 0 or 1; Y is $C_1$–$C_4$ alkylene, and z is 0 or 1; and $R^1$ is H, lower alkyl, or $R_f$—X—$Y_z$.

Some of the advantages of the compounds of the invention include: application of the compounds of the invention to a surface is relatively fast and simple which minimizes cost and environmental impact; dense films or layers can be formed using very small amounts of the compound; compounds of the invention self-assemble into protective layers; and the protective layers can be very durable depending upon the surface type and compound used.

DETAILED DESCRIPTION OF THE INVENTION

Figure 1:
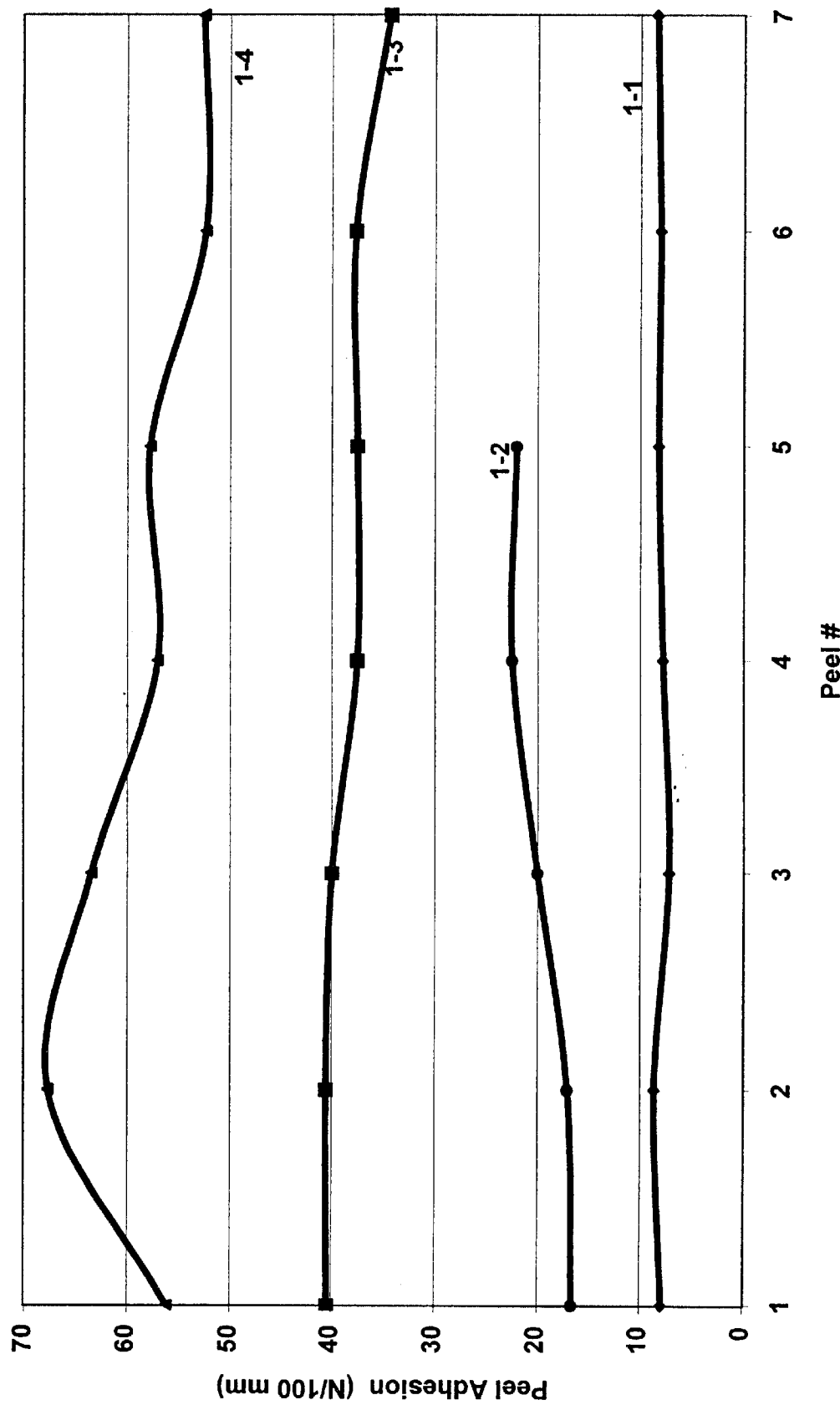
FIG. 1 is a graphical depiction of the Peel Adhesion Values shown in Table 1 for Scotch™ Brand Magic™ Tape.

"Metallic surface" refers to surface coated or formed from a metal or a metal alloy which may also contain a metalloid. "Metal" refers to an element such as iron, gold, aluminum, etc., generally characterized by ductility, malleability, luster, and conductivity of heat and electricity which forms a base with the hydroxyl radical and can replace the hydrogen atom of an acid to form a salt. "Metalloid" refers to nonmetallic elements having some of the properties of a metal and/or forming an alloy with a metal (for example, semiconductors) and also includes nonmetallic elements which contain metal and/or metalloid dopants. "Release agent" refers to a compound or composition which imparts a release characteristic to a surface. "Lower alkyl" group means an alkyl group having from 1 to 5 carbon atoms.

The fluoroaliphatic radical $R_f$, is a fluorinated, stable, inert, non-polar, monovalent moiety which is both oleophobic and hydrophobic. While $R_f$ can have a large number of carbon atoms, compounds where $R_f$ is not more than 22 carbon atoms are preferred since large radicals represent less efficient utilization of fluorine than is possible with smaller $R_f$ radicals. The skeletal chain of $R_f$ can be straight or branched and can be composed of only carbon, hydrogen, and fluorine, or only carbon and fluorine. Generally, $R_f$ will have 1 to 22 carbon atoms, preferably at least 3, and more preferably about 6 to about 12 and will contain from about 40 to about 83 weight percent, and preferably from about 40 to about 74 weight percent, fluorine. Preferably, the terminal portion of the moiety is a perfluorinated moiety which preferably contains at least 3 carbon atoms. The preferred compounds are those in which $R_f$ is substantially completely fluorinated, for example, where $R_f$ is $C_nF_{2n+1}$—$(CH_2)_m$—, and where m is 2.

X may be a covalent bond, —CO$_2$—, —SO$_3$—, —CONH—, —SO$_2$NR—, —O—, —S— or —NR—, wherein R is H or C$_1$ to C$_5$ alkylene. Y may be methylene or a covalent bond. R$^1$ may be a hydrogen atom, lower alkyl, or R$_f$—X—Y— as described above and is preferably a hydrogen atom. Preferably, the R$_f$—X—Y— moiety is located at the number 5 carbon of the benzotriazole molecule.

Compounds of the invention can be generally obtained by reacting benzotriazoles with fluoro-alcohols. The reaction is generally carried out in solution with the triazole and the alcohol being dissolved in a suitable solvent. Useful triazole solvents include trifluoromethanesulfonic acid and toluene. The reaction is conducted at a temperature of from about 100 to about 120° C. in an inert gaseous atmosphere. The reaction mixture is cooled, the isolated precipitate is re-dissolved in a suitable solvent, the pH is adjusted to alkaline and the solvent evaporated. Optionally, the material can be purified using known techniques such as fractional sublimation.

The compounds of the invention will form substantially continuous monolayer films on metal or metalloid surfaces by simply contacting the compound(s) with the surface to be treated. The molecules form "substantially continuous monolayer" films meaning that the individual molecules pack together as densely as their molecular structures allow. It is believed that the films self assemble in that the triazole groups of the molecules of the invention attach to available areas of the metal/metalloid surface and that the pendent fluorocarbon tails are aligned substantially towards the external interface.

The effectiveness of a monolayer film and the degree to which a monolayer film is formed on a surface is generally dependent upon the strength of the bond between the compound and the particular metal or metalloid surface and the conditions under which the film-coated surface is used. For example, some metal or metalloid surfaces may require a highly tenacious monolayer film while other such surfaces require monolayer films having much lower bond strength. Useful metal and metalloid surfaces include any surface that will bond with compounds of the invention and preferably, form a monolayer or a substantially continuous monolayer film. Examples of suitable surfaces for forming said monolayer films include those comprising copper, nickel, chromium, zinc, silver, germanium, and alloys thereof.

The monolayer or substantially continuous monolayer films of the invention may be formed by contacting a surface with an amount of the compound or compounds of the invention sufficient to coat the entire surface. The compound may be dissolved in an appropriate solvent, the composition applied to the surface, and allowed to dry. Suitable solvents include ethyl acetate, 2-propanol, acetone, water and mixtures thereof. Alternatively, the compounds of the present invention may be deposited onto a surface from the vapor phase. Any excess compound may be removed by rinsing the substrate with solvent and/or through use of the treated substrate.

The fluorochemical benzotriazoles of the invention are particularly useful as release agents for metal or metalloid surfaces or substrates. Specific uses include as release agents for pressure sensitive adhesive tape release backings and for molds. The compositions of the invention may also be used as a corrosion inhibitor for metal or metalloid surfaces.

EXAMPLES

The features and advantages of the present invention are illustrated in the following examples which incorporate particular materials and amounts, and should not be construed to unduly limit this invention. All materials are commercially available unless otherwise stated or apparent. All parts, percentages, ratios and the like in the examples are by weight unless otherwise indicated.

Example 1

1H,1H,2H,2H-perfluorododecyl benzotriazole-5-carboxylic acid ester was prepared as follows:

A mixture of benzotriazole-5-carboxylic acid (3.5 g, available from Aldrich Chemical Co., Inc, Milwaukee, Wis.) and trifluoromethanesulfonic acid ("Triflic" acid, approximately 12 g, available from Minnesota Mining & Manufacturing Company, St. Paul, Minn.) was heated at approximately 90° C., with stirring, until a homogeneous solution was obtained (approximately 1 hour). 1H,1H,2H,2H-perfluorododecyl alcohol (11.58 g, available from PCR Chemicals, Gainesville, Fla.) was melted and added to the reaction mixture along with 18 mL of dry toluene. The resulting reaction mixture was heated to 105–110° C. under a nitrogen atmosphere for approximately 14 hours and cooled to ambient temperature. The cooled reaction mixture was poured over crushed ice (approximately 400 g), the resulting mixture vigorously agitated to break up larger lumps of the precipitated product and the solid product isolated by filtration after the ice had melted. The isolated product was dissolved in tetrahydrofuran (THF, 500 mL), about 50 mL of water were added to the solution, and methanolic potassium hydroxide (1 N) was added in rapid, dropwise fashion to increase the pH of the solution to about 8–9 (as determined by pH paper). The sides of the reaction container were washed with water (about 100–150 mL) and the resulting mixture stirred under a nitrogen stream to evaporate the THF. After most of the THF had evaporated (approximately 2.5 hours) the product was present as a frothy precipitate in approximately 200 mL of water. The solid product was isolated by filtration, rinsed with several aliquots (approximately 100 mL) of water, and air-dried overnight. The crude material was purified by fractional sublimation at approximately 115° C. and 10$^{-6}$ Torr (133× 10$^{-6}$ Pa). A waxy solid, consisting of a mixture of unreacted alcohol and traces of water and solvent, which collected on the finger of the sublimator after three to five hours was removed and the sublimation continued at 167–171° C. to produce purified 1H,1H,2H,2H-perfluorododecyl benzotriazole-5-carboxylic acid ester (BTA-FCE-12) as a faintly pink/white solid having a melting point of 171° C. The NMR (H$^1$, C$^{13}$, F$^{19}$), infrared, and GC/MS spectra of the purified material were consistent with the following structure:

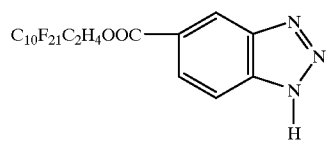

BTA-FCE-12

Example 2

An approximately 4:3:1 mixture of 1H,1H,2H,2H-perfluorotetradecyl benzotriazole-5-carboxylic acid ester (BTA-FCE-14), 1H,1H,2H,2H-perfluorododecyl benzotriazole-5-carboxylic acid ester (BTA-FCE-12), and 1H,1H,2H,2H-perfluorodecyl benzotriazole-5 -carboxylic acid ester (BTA-FCE -10) were prepared substantially using the procedure described for the preparation of 1H,1H,2H,2H-perfluorododecyl benzotriazole-5-carboxylic acid ester described in Example 1 except that an approximately 4:3:1 mixture of 1H,1H,2H,2H-perfluorotetradecyl alcohol, 1H,1H,2H,2H-perfluorododecyl alcohol, and 1H,1H,2H,2H-perfluorodecyl alcohol ( 12 g, available from Daikin Chemical, Tokyo, Japan) was substituted for 1H,1H,2H,2H-perfluorododecyl alcohol. The above mixture of BTA-FCE-14, BTA-FCE-12, and BTA-FCE-10 was obtained as a pink/white solid. The NMR ($H^1$, $C^{13}$, $F^{19}$), and GC/MS spectra of the purified material were consistent with the following structures:

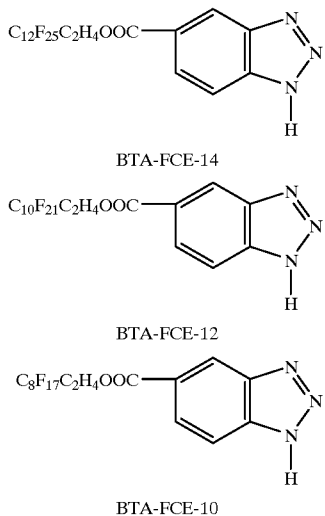

BTA-FCE-14

BTA-FCE-12

BTA-FCE-10

Example 3

1H,1H,2H,2H-perfluorodecyl benzotriazole-5-carboxylic acid ester was prepared substantially using the procedure described for the preparation of 1H,1H,2H,2H-perfluorododecyl benzotriazole-5-carboxylic acid ester described in Example 1 except that 1H,1H,2H,2H-perfluorodecyl alcohol (9.3 g, available from PCR Chemicals) was substituted for 1H,1H,2H,2H-perfluorododecyl alcohol. The 1H,1H,2H,2H-perfluorodecyl benzotriazole-5-carboxylic acid ester (BTA-FCE-10) was obtained as a pink/white solid having a melting point of 143–145° C. The NMR ($H^1$, $C^{13}$, $F^{19}$), infrared, and GC/MS spectra of the purified material were consistent with the following structure:

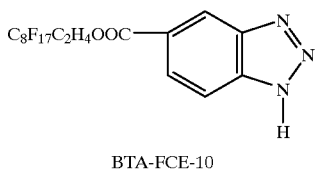

BTA-FCE-10

Example 4

1H,1H,2H,2H-perfluorooctyl benzotriazole-5-carboxylic acid ester was prepared substantially using the procedure described for the preparation of 1H,1H,2H,2H-perfluorododecyl benzotriazole-5-carboxylic acid ester described in Example 1 except that 1H,1H,2H,2H-perfluorooctyl alcohol (7.3g, available from PCR Chemicals) was substituted for 1H,1H,2H,2H-perfluorododecyl alcohol. The 1H,1H,2H,2H-perfluorooctyl benzotriazole-5-carboxylic acid ester (BTA-FCE-8) was obtained as a pink/white solid having a melting point of 118–122° C. The NMR ($H^1$, $C^{13}$, $F^9$), infrared, and GC/MS spectra of the purified material were consistent with the following structure:

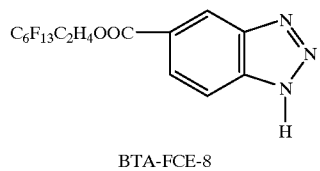

BTA-FCE-8

Example 5

1H,1H,2H,2H-perfluorohexyl benzotriazole-5-carboxylic acid ester was prepared substantially using the procedure described for the preparation of 1H,1H,2H,2H-perfluorododecyl benzotriazole-5-carboxylic acid ester described in Example 1 except that 1H,1H,2H,2H-perfluorohexyl alcohol (5.3 g, available from PCR Chemicals) was substituted for 1H,1H,2H,2H-perfluorododecyl alcohol. The 1H,1H,2H,2H-perfluorohexyl benzotriazole-5-carboxylic acid ester (BTA-FCE-6) was obtained as a pink/white solid having a melting point of 105–107° C. The NMR ($H^1$, $C^{13}$, $F^{19}$), infrared, and GC/MS spectra of the purified material were consistent with the following structure:

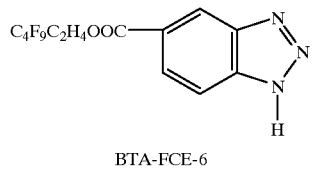

BTA-FCE-6

Example 6

The ability of 1H,1H,2H,2H-perfluorododecyl benzotriazole-5-carboxylic acid ester to react with and change the surface properties of copper was studied using a standard test for peel adhesion, ASTM D 3330-96, except that tape samples were repeatedly applied over the same area of the test coupon, using the peel strength as an indicator of the substantivity of the release treatment to the copper surface.

Adhesion test coupons (20.3 by 5.1 cm) were prepared from a 3.2 mm thick copper plate (hot rolled copper sheet, ASTM B 152 Alloy 110, soft M20 temper, Central Steel & Wire Co., Chicago, Ill.). Each test coupon was surface finished using a hand-held sander and progressively finer sandpaper (3M WETORDRY™ TRI-M-ITE™ 280, 600 and 1200 grit, available from Minnesota Mining & Manufacturing Company, St. Paul, Minn.) for three minutes each stage. Immediately prior to applying a release treatment to the test coupon, the coupon was cleaned by wiping it with a heptane saturated wipe (Kimwipes® Extra Low Lint Wiper #34256, available from Kimberley Clark Corp, Roswell, Ga.) followed by wiping with an ethanol saturated wipe. BTA-FCE-12, prepared as described above, was applied to the surface of two clean test coupons by placing the coupons in a 10.2 cm diameter by 25.4 cm tall evacuable glass chamber together with 29 mg of the BTA-FCE-12, the apparatus evacuated to $10^{-7}$ Torr ($133\times10^{-7}$ Pa) and the evacuated chamber placed in a circulating air oven maintained at 150° C. for 3.5 hours.

Benzotriazole (BTA) was applied to a third test coupon by heating the coupon under vacuum ($10^{-7}$ Torr ($133\times10^{-7}$ Pa)) with 50.3 mg BTA at 150° C. for 1.5 hours to provide a comparative reactive surface treatment.

A fourth test coupon was treated with a silicone release material by spray-coating the coupon with a linear poly (dimethylsiloxane) mold release agent, IMS S312-A (available from IMS, Chagrin Falls, Ohio.) to provide comparison with a non-reactive surface treatment.

A test coupon which had been cleaned using the solvent saturated wipe techniques described above served as a control.

The adherence of a strip of pressure-sensitive adhesive tape to the treated and control copper coupons described above was directly measured under conditions described in ASTM Standard D 3330-96. The tape was applied to the test coupon as specified in the test procedure and subsequently peeled from the surface at a 180° angle at a rate of 38.1 mm per second using a constant-rate-of-extension adhesion tester manufactured by Instrumentors Inc., Strongsville, Ohio. All tape and the copper test coupons were conditioned at 50% relative humidity and 23° C. for 24 hours prior to testing, and all peel tests were performed under these environmental conditions.

Two commercially-available pressure-sensitive adhesive tapes, Scotch™ Brand Magic™ Tape #810 (available from Minnesota Mining & Manufacturing Co.), having an acrylate based adhesive, and Highland™ Brand Packaging Tape #371 (Available from Minnesota Mining & Manufacturing Co.), having a Kraton™ based adhesive, were used in the adhesion testing.

Figure 2:
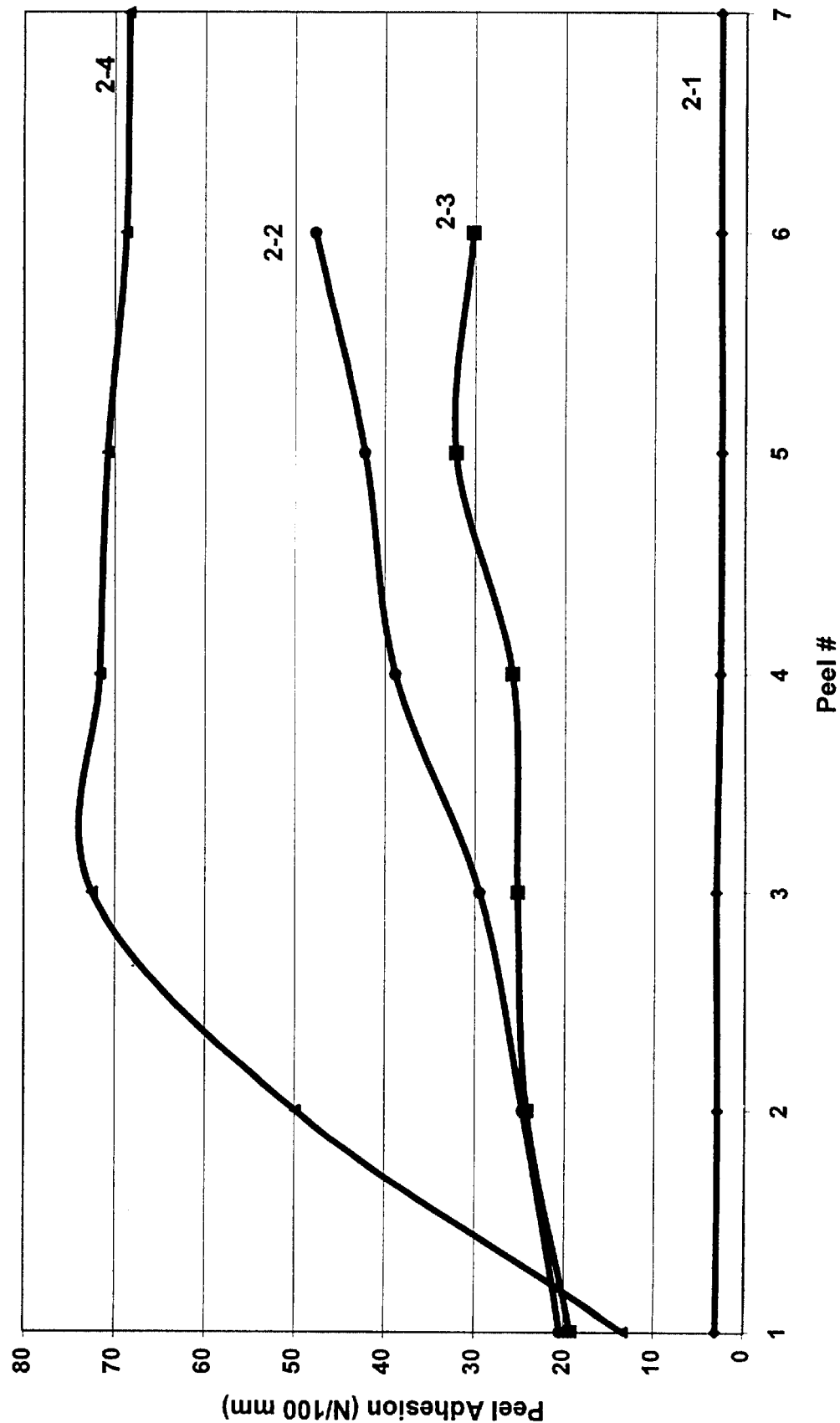
FIG. 2 is a graphical depiction of the Peel Adhesion Values shown in Table 1 for Highland™ Brand Packaging Tape.

Representative peel adhesion data are summarized in Table 1. Graphs depicting the data series in these two tables are shown in FIGS. 1 and 2. Curves 1-1 and 2-1 depict the peel adhesion data for BTA-FCE-12 treated copper; curves 1-2 and 2-2 depict the peel adhesion data for silicone treated copper; curves 1-3 and 2-3 depict the peel adhesion data for untreated copper; and curves 1-4 and 2-4 depict the peel adhesion data for BTA treated copper. BTA-FCE-12 modifies the copper surface to give values of peel adhesion that are appreciably lower than the control copper surface or copper treated with a silicone release agent or treated with the parent benzotriazole.

TABLE 1

Peel Adhesion Values

| Substrate | Scotch ™ Brand Magic ™ Tape | | Highland ™ Brand Packaging Tape | |
| --- | --- | --- | --- | --- |
| | Peel # | Peel (N/100 mm) | Peel # | Peel (N/100 mm) |
| Untreated Copper | 1 | 40.4 | 1 | 19.3 |
| | 2 | 40.6 | 2 | 24.2 |
| | 3 | 40.0 | 3 | 25.2 |
| | 4 | 37.5 | 4 | 25.8 |
| | 5 | 37.5 | 5 | 32.1 |
| | 6 | 37.7 | 6 | 30.2 |
| | 7 | 34.3 | | |
| BTA-FCE-12 Treated | 1 | 7.9 | 1 | 3.1 |
| | 2 | 8.6 | 2 | 2.9 |

TABLE 1-continued

Peel Adhesion Values

| Substrate | Scotch ™ Brand Magic ™ Tape | | Highland ™ Brand Packaging Tape | |
| --- | --- | --- | --- | --- |
| | Peel # | Peel (N/100 mm) | Peel # | Peel (N/100 mm) |
| Copper | 3 | 7.2 | 3 | 3.1 |
| | 4 | 7.7 | 4 | 2.6 |
| | 5 | 8.2 | 5 | 2.5 |
| | 6 | 8.0 | 6 | 2.6 |
| | 7 | 8.3 | 7 | 2.6 |
| Silicone Mold Release Treated Copper | 1 | 16.6 | 1 | 20.4 |
| | 2 | 17.1 | 2 | 24.7 |
| | 3 | 20.0 | 3 | 29.5 |
| | 4 | 22.5 | 4 | 38.8 |
| | 5 | 22.0 | 5 | 42.2 |
| | | | 6 | 47.7 |
| BTA Treated Copper | 1 | 56.2 | 1 | 13.4 |
| | 2 | 67.7 | 2 | 49.9 |
| | 3 | 63.5 | 3 | 72.5 |
| | 4 | 57.1 | 4 | 71.7 |
| | 5 | 57.8 | 5 | 70.8 |
| | 6 | 52.4 | 6 | 68.7 |
| | 7 | 52.5 | 7 | 68.4 |

Example 7

The ability of 1H,1H,2H,2H-perfluorododecyl benzotriazole-5-carboxylic acid ester to react with and change the surface properties of copper was studied by examining its ability to inhibit corrosion of the copper surface.

Soft rolled alloy 110 copper foil having a caliper of 0.00343 cm and purity greater than 99.90% was used for the corrosion inhibition tests. The copper was cleaned as previously described, using the solvent saturated wipe, and cut into 5 cm×10 cm test coupons.

One test coupon was treated with BTA-FCE-12 by placing it inside a 6.0 cm diameter by 22.0 cm tall evacuable glass chamber, together with 35.4 mg of BTA-FCE-12, the chamber evacuated to $1\times10^{-7}$ Torr ($133\times10^{-7}$ Pa), and the evacuated chamber placed in a circulating air oven maintained at 150° C. for one hour.

A second test coupon was treated with 44.0 mg benzotriazole(BTA) using substantially the same procedure, except that the oven was maintained at 100° C., to provide a comparative reactive surface treatment.

Copper foil that had been cleaned using the solvent saturated wipe techniques described above served as a control.

Five-centimeter by three-centimeter samples of the BTA-FCE-12 and BTA treated copper, and a control, were positioned in a non-overlapping configuration inside a 12.7 cm×20.3 cm polyethylene bag, the bag sealed, 100 microliters of hydrogen sulfide gas injected directly through the wall of the bag, the puncture sealed with adhesive tape, and the surface of the samples observed for color change due to sulfide formation. Only the control was seen to change, becoming a dark red to purple within an hour.

The samples were removed from the bag after one hour and the surface on each was analyzed using x-ray photoelectron spectroscopy (XPS or ESCA) using a Model SSX-100-01 M-Probe™ ESCA Spectrometer (available from Surface Science Laboratories, Mountain View, Calif.) which makes use of an $Al_{K\alpha}$ monochromatic x-ray excitation source and a hemispherical energy analyzer. The photoelectron take-off angle for all spectra recorded was 38° measured with respect to the surface normal. The area analyzed on each was 200 μm×750 μm. The pressure in the vacuum system during analysis was maintained at or below $2.7 \times 10^{-7}$ Pa.

A survey spectrum was recorded on each sample surface (0 eV–1100 eV binding energy/2200 data points/100 milliseconds dwell time per data point per scan×8 scans). The atomic percent concentrations of carbon, oxygen, nitrogen, copper, fluorine, and sulfur on each surface were calculated by measuring the areas of the $C(1s_{1/2})$, $O(1s_{1/2})$, $N(1s_{1/2})$, $Cu(2p_{3/2})$, $F(1s_{1/2})$ and $S(2p_{3/2,1/2})$ photoelectron peaks. in each survey spectrum and dividing each by the appropriate relative sensitivity factor provided in the data reduction software supplied by the instrument manufacturer. All calculations were made ignoring the presence of hydrogen which cannot be detected by this technique. The information obtained from these analyses is summarized in Table 2.

The data show that the BTA-FCE-12 treated surface has no sulfur present at a detectable level while the BTA and untreated copper surfaces show evidence for the incorporation of sulfur after the $H_2S$ exposure. The detection limit for sulfur on this type of surface is approximately 0.08 atomic % (signal:noise is 2.0). The binding energy of the $S(2p_{3/2})$ peak on the untreated and BTA treated copper samples after exposure to $H_2S$ is between 162 and 163 eV, matching those given in the NIST XPS Database for $Cu_2S$ (NIST Standard Reference Database #20— Version 2.0, U.S. Department of Commerce, National Institute of Standards and Technology, Gaithersburg, Md.).

TABLE 2

Elements Present at a Detectable Level on Each Copper Surface by XPS (ESCA).

| Sample Description | Atomic % Concentration | | | | | |
|---|---|---|---|---|---|---|
| | C | O | N | Cu | F | S |
| Control Samples - No Exposure to $H_2S$ | | | | | | |
| Untreated Copper | 50.5 | 22.9 | n.d. | 26.6 | n.d. | n.d. |
| BTA-FCE-12 Treated Copper | 39.0 | 3.1 | 3.8 | 0.9 | 53.2 | n.d. |
| BTA Treated Copper | 65.4 | 0.9 | 24.8 | 8.9 | n.d. | n.d. |
| Exposed to 100 μL $H_2S$ for 1 Hour | | | | | | |
| Untreated Copper | 58.8 | 7.0 | n.d. | 19.6 | n.d. | 14.6 |
| BTA-FCE-12 Treated Copper | 39.1 | 3.3 | 3.9 | 0.9 | 52.8 | n.d. |
| BTA Treated Copper | 63.2 | 2.1 | 25.3 | 8.6 | n.d. | 0.8 | n.d. is not detectable

The various modifications and alterations of this invention will be apparent to those skilled in the art without departing from the scope and spirit of this invention and this invention should not be restricted to that set forth herein for illustrative purposes.

What is claimed is:

1. A fluorochemical benzotriazole having the formula:

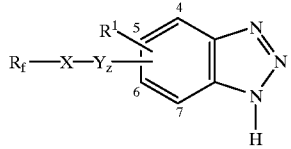

wherein $R_f$ is $C_nF_{2n+1}$—$(CH_2)_m$—, wherein n is 1 to 22 and m is 0, or an integer from 1 to 3; X is —$CO_2$—, —$SO_3$—, —CONH—, —O—, —S—, a covalent bond, —$SO_2NR$—, or wherein R is H or $C_1$ to $C_5$ alkylene;

Y is —$CH_2$— wherein z is 0 or 1; and $R^1$ is H lower alkyl or $R_f$—X—$Y_z$— with the provisos that when X is —S— or —O—, m is 0, and z is 0, n is $\geq 7$ and when X is a covalent bond, m or z is at least 1.

2. The fluorochemical benzotriazole according to claim 1 wherein $R^1$ is H.

3. The fluorochemical benzotriazole according to claim 1 wherein z is 0.

4. The fluorochemical benzotriazole according to claim 4 wherein X is —$CO_2$—, —$SO_3$—, —O—, —NR—, —$SO_2NR$—, —NR—, or —S—.

5. the fluorochemical benzotriazole according to claim 1 wherein m is 2 and z is 0.

6. The fluorochemical benzotriazole according to claim 5 wherein X is —$CO_2$—.

7. The fluorochemical benzotriazole according to claim 6 wherein n is 10.

8. The fluorochemical according to claim 1 wherein n is at least 6 and wherein n+m ranges from 8 to 20.

9. A composition for imparting release or corrosion inhibition properties to a metal or metalloid surface comprising one or more of the compounds of claim 1.

10. The composition of claim 9 wherein said composition comprises two or more compounds of the formula of claim 1.

11. The composition of claim 9 further containing a solvent.

12. The composition of claim 9 used as a release agent or a corrosion inhibitor.

13. A method of forming an adherent film on a metallic or a metalloid surface comprising the step of contacting a composition comprising a fluorochemical benzotriazole according to claim 1 with said surface.

14. The method of claim 13 wherein said composition further comprises a solvent.

15. The method of claim 13 wherein said composition is in the form of a solution or a vapor.

16. A film comprising a plurality of molecules of one or more fluorochemical banzotriazoles according co claim 1 bonded to a metallic or non-metallic surface wherein said plurality of molecules forms a self-assembled film that is a substantially continuous monolayer.

17. An article comprising a metallic or a metalloid surface having a self-assembled film adhered to said surface, said film comprising a plurality of molecules of one or more fluorochemical benzotriazole of claim 1 adhered to said surface.

18. A release agent in the form of a film comprising a plurality of molecules of one or more fluorochemical benzotriazoles according to claim 1 bonded to a metallic or non-metallic surface wherein said plurality of molecules forms a self-assembled film that is a substantially continuous monolayer.

19. The fluorochemical benzotriazole of claim 1 wherein n is 4 to 12.

20. The fluorochemical benzotriazole of claim 1 wherein n is 3 to 12.

21. An article having a release surface comprising a metallic or a metalloid surface having a self-assembled film adhered to said surface, said film comprising a plurality of molecules of one or more fluorochemical benzotriazoles having the formula:

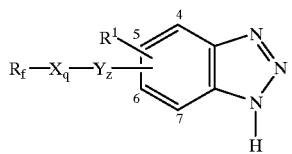

wherein $R_f$ is $C_nF_{2n+1}$—$(CH_2)_m$—, n is 1 to 22, m is 0 or an integer from 1 to 3:

$X_q$ is —$CO_2$—, —$SO_3$—, —S—, —O—, —CONH—, a covalent bond, —$SO_2NR$—, or —NR— wherein R is H or $C_1$ to $C_5$ alkylene, and q is 0 or 1;

Y is $C_1$–$C_4$ alkylene, and z is 0 or 1; and $R^1$ is H, lower alkyl, or $R_f$—X—$Y_z$ adhered to said surface.

22. A method of imparting corrosion inhibition or release properties to a metallic or a metalloid surface comprising the step of contacting a composition comprising a fluorochemical benzotriazole having the formula:

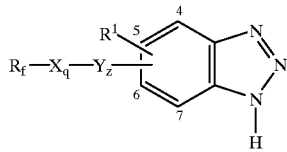

wherein $R_f$ is $C_nF_{2n+1}$—$(CH_2)_m$—, n is 1 to 22, m is 0 or an integer from 1 to 3;

$X_q$ is —$CO_2$—, —$SO_3$—, —S—, —O—, —CONH— a covalent bond, —$SO_2NR$— or —NR— wherein R is H or $C_1$ to $C_5$ alkylene, and q is 0 or 1;

Y is $C_1$–$C_4$ alkylene and z is 0 or 1; and $R^1$ is H. lower alkyl or $R_f$—X—$Y_z$ with said surface.

23. A fluorochemical benzotriazole having the formula:

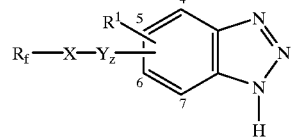

wherein $R_f$ is $C_nF_{2n+1}$—$(CH_2)_m$—, wherein n is 6 to 22 and m is 0, or an integer from 1 to 3;

X is —$CO_2$—, —$SO_3$—, —CONH—, —O—, —S—, a covalent bond, —$SO_2NR$—, or —NR—, wherein R is H or $C_1$ to $C_5$ alkylene;

Y is —$CH_2$— wherein z is 0 or 1; and $R^1$ is H, lower alkyl or $R_f$—X—$Y_z$— with the provisos that when X is —S— or —O—, m is 0, and z is 0, n is $\geq 7$ and when X is a covalent bond, m or z is at least 1.

24. The fluorochemical benzotriazole according to claim 23 wherein $R^1$ is H.

25. The fluorochemical benzotriazole according to claim 23 wherein X is —$C_2$—, —$S_3$—, —O—, —NR—, —$SO_2NR$—, —NR—, or —S—.

26. The fluorochemical benzotriazole according to claim 23 wherein X is —$CO_2$—.

27. A composition for imparting release or corrosion inhibition properties to a metal or metalloid surface comprising one or more of the compounds of claim 23.

28. The composition of claim 27 further comprising a solvent.

29. A film comprising a plurality of molecules of one or more fluorochemical benzotriazoles according to claim 23 bonded to a metallic or non-metallic surface wherein said plurality of molecules forms a self-assembled film that is a substantially continuous monolayer.

30. An article comprising a metallic or a metalloid surface having a self-assembled film adhered to said surface, said film comprising a plurality of molecules of one or more fluorochemical benzotriazole of claim 23 adhered to said surface.

31. A method of forming an adherent film on a metallic or a metalloid surface comprising the step of contacting a composition comprising a fluorochemical benzotriazole according to claim 23 with said surface.

* * * * *